(12) United States Patent
Parkins

(10) Patent No.: US 9,774,946 B2
(45) Date of Patent: *Sep. 26, 2017

(54) WIRELESS EARPLUG WITH IMPROVED SENSITIVITY AND FORM FACTOR

(71) Applicant: Red Tail Hawk Corporation, Philadelphia, PA (US)

(72) Inventor: John W. Parkins, Philadelphia, PA (US)

(73) Assignee: Red Tail Hawk Corporation, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/334,497

(22) Filed: Oct. 26, 2016

(65) Prior Publication Data

US 2017/0041700 A1 Feb. 9, 2017

Related U.S. Application Data

(63) Continuation of application No. 14/186,477, filed on Feb. 21, 2014, now Pat. No. 9,516,404, which is a (Continued)

(51) Int. Cl.
*H04R 1/10* (2006.01)
*H04M 1/05* (2006.01)
(Continued)

(52) U.S. Cl.
CPC ............ *H04R 1/1075* (2013.01); *H04M 1/05* (2013.01); *H04M 1/215* (2013.01); (Continued)

(58) Field of Classification Search
CPC .. H04R 1/1091; H04R 1/1041; H04R 1/1075; H04R 1/1016; H04R 2209/041; H04R 3/08; H04R 2420/07; A61F 11/08; A61F 11/14; H04M 1/05; H04M 1/215; H04M 1/6066
(Continued)

(56) References Cited

U.S. PATENT DOCUMENTS 2,048,604 A 7/1936 Finch
2,268,665 A 1/1942 Loewe
(Continued)

FOREIGN PATENT DOCUMENTS

DE 3508830 A1 9/1986
DE 3826294 A1 2/1990
WO 2006042298 A2 4/2006

OTHER PUBLICATIONS

Knowles Acoustic ED Series Speaker Specification. Dec. 2003.
(Continued)

*Primary Examiner* — David Ton
(74) *Attorney, Agent, or Firm* — Brown & Michaels, PC

(57) ABSTRACT

An improved wireless communications earplug for use with a magnetic field transmitter. The wireless earplug has a receiver made of a coil of wire on a magnetic bobbin, mounted in close proximity or in contact with a magnetic case of a speaker. The magnetic case of the speaker serves to increase the magnetic flux through the receiver and improves the efficiency of the earplug. The speaker is acoustically coupled to an eartip, and the earplug may be molded into a custom earplug body.

22 Claims, 7 Drawing Sheets

Related U.S. Application Data continuation of application No. 12/832,363, filed on Jul. 8, 2010, now Pat. No. 8,693,720, which is a continuation-in-part of application No. 11/837,129, filed on Aug. 10, 2007, now Pat. No. 8,688,036.

(60) Provisional application No. 61/224,531, filed on Jul. 10, 2009, provisional application No. 60/824,091, filed on Aug. 31, 2006.

(51) Int. Cl.

| | | |
|---|---|---|
| *H04M 1/215* | (2006.01) | |
| *H04M 1/60* | (2006.01) | |
| *A61F 11/08* | (2006.01) | |
| *A61F 11/14* | (2006.01) | |
| *H04R 3/08* | (2006.01) | |

(52) U.S. Cl.
CPC ........ *H04M 1/6066* (2013.01); *H04R 1/1016* (2013.01); *H04R 1/1041* (2013.01); *H04R 1/1091* (2013.01); *A61F 11/08* (2013.01); *A61F 11/14* (2013.01); *H04R 3/08* (2013.01); *H04R 2209/041* (2013.01); *H04R 2420/07* (2013.01)

(58) Field of Classification Search
USPC ........ 381/326–331, 315, 312, 322, 74, 23.1
See application file for complete search history.

(56) References Cited

U.S. PATENT DOCUMENTS

| | | | |
|---|---|---|---|
| 2,530,621 | A | 11/1950 | Lybarger et al. |
| 3,125,646 | A | 3/1964 | Lewis |
| 3,322,897 | A | 5/1967 | Vozeolas et al. |
| 3,752,939 | A | 8/1973 | Bartz |
| 4,150,262 | A | 4/1979 | Ono |
| 4,957,478 | A | 9/1990 | Maniglia |
| 4,972,491 | A | 11/1990 | Wilcox, Jr. |
| 5,073,947 | A | 12/1991 | Reddemann et al. |
| 5,343,532 | A | 8/1994 | Shugart, III |
| 5,396,563 | A | 3/1995 | Yoshimi |
| 5,420,930 | A | 5/1995 | Shugart, III |
| 5,701,348 | A | 12/1997 | Shennib et al. |
| 5,796,821 | A | 8/1998 | Crouch et al. |
| 6,012,812 | A | 1/2000 | Rickards |
| 6,078,675 | A | 6/2000 | Bowen-Nielsen et al. |
| 6,208,740 | B1 | 3/2001 | Grever |
| 6,438,245 | B1 | 8/2002 | Taenzer et al. |
| 6,694,034 | B2 | 2/2004 | Julstrom et al. |
| 6,823,171 | B1 | 11/2004 | Kaario |
| 6,925,179 | B2 | 8/2005 | Waldron et al. |
| 7,206,426 | B1 | 4/2007 | Julstrom et al. |
| 7,426,279 | B2 | 9/2008 | Cochran et al. |
| 7,680,292 | B2 | 3/2010 | Warren et al. |
| 8,116,494 | B2 | 2/2012 | Rass |
| 8,693,720 | B2 | 4/2014 | Parkins |
| 2002/0061113 | A1 | 5/2002 | van Halteren et al. |
| 2002/0141545 | A1 | 10/2002 | Segovia |
| 2003/0031339 | A1 | 2/2003 | Marshall et al. |
| 2003/0219135 | A1 | 11/2003 | Morimoto |
| 2004/0151334 | A1 | 8/2004 | Vaudrey et al. |
| 2004/0258261 | A1 | 12/2004 | Cochran et al. |
| 2005/0018859 | A1 | 1/2005 | Buchholz |
| 2005/0078848 | A1 | 4/2005 | Hlibowicki |
| 2005/0094830 | A1 | 5/2005 | Stanley |
| 2005/0245213 | A1 | 11/2005 | Hirano et al. |
| 2005/0260953 | A1 | 11/2005 | Lefler et al. |
| 2006/0013420 | A1 | 1/2006 | Sacha |
| 2006/0269088 | A1 | 11/2006 | Julstrom et al. |
| 2007/0041602 | A1 | 2/2007 | Killion |
| 2007/0041606 | A1 | 2/2007 | Sheppard |
| 2007/0149261 | A1 | 6/2007 | Huddart |
| 2007/0153444 | A1 | 7/2007 | Groh et al. |
| 2008/0025524 | A1 | 1/2008 | Vaudrey et al. |
| 2008/0132193 | A1 | 6/2008 | Petrovic et al. |
| 2009/0041285 | A1 | 2/2009 | Parkins et al. |
| 2009/0143097 | A1 | 6/2009 | Wilson |
| 2010/0014700 | A1 | 1/2010 | Zhou et al. |
| 2010/0016827 | A1 | 1/2010 | Hunter et al. |
| 2010/0278371 | A1 | 11/2010 | Hanada |
| 2010/0296667 | A1 | 11/2010 | Parkins |
| 2011/0081936 | A1 | 4/2011 | Haim et al. |
| 2011/0103605 | A1 | 5/2011 | Killion et al. |
| 2011/0130622 | A1 | 6/2011 | Ilberg |
| 2012/0021704 | A1 | 1/2012 | Chan et al. |
| 2012/0275638 | A1 | 11/2012 | Chang |
| 2012/0322378 | A1 | 12/2012 | Tai |
| 2013/0244722 | A1 | 9/2013 | Rousu et al. |
| 2014/0087659 | A1 | 3/2014 | Parkins |
| 2014/0295909 | A1 | 10/2014 | Ouchi et al. |

OTHER PUBLICATIONS

Viking Chip Common Mode Choke-CM Series. Apr. 2006.
Van Wiljngaarden et al. "Development of the Wireless "Communications Earplug" for application in Military Aviation" J. Audio Eng. Soc., vol. 48, No. 6, Jun. 2000.
James et al. "Protecting Crew Members against Military Vehicle Noise." Presented at the RTO AVT Symposium and published in RTO-MP-AVT-110; pp. 1-18; Oct. 2004.
Sjsu "Electromagnetic Induction", http://www.physics.sjsu.edu/becker/physics51/induction.htm; pp. 1-23; Jan. 2007.

US 9,774,946 B2

WIRELESS EARPLUG WITH IMPROVED SENSITIVITY AND FORM FACTOR

REFERENCE TO RELATED APPLICATIONS

This application is a continuation of co-pending application Ser. No. 14/186,477, filed Feb. 21, 2014, entitled "Wireless Earplug with Improved Sensitivity and Form Factor", published as publication number 2014/0301563, which was a continuation of co-pending application Ser. No. 12/832,363, filed Jul. 8, 2010, entitled "Wireless Earplug with Improved Sensitivity and Form Factor", published as publication number 2010/0296667, which claimed benefit of Provisional Application No. 61/224,531, filed Jul. 10, 2009, entitled "Wireless Earplug with Improved Sensitivity and Form Factor", and which was a continuation-in-part of copending U.S. application Ser. No. 11/837,129, entitled "Wireless Communications Headset System Employing a Loop Transmitter That Fits Around the Pinna", filed Aug. 10, 2007, and published on Feb. 12, 2009, as US2009/0041285, which claimed the benefit of Provisional Application No. 60/824,091, filed Aug. 31, 2006, entitled "Wireless Communications System Employing a Loop Transmitter That Fits Around The Pinna". The aforementioned applications are hereby incorporated herein by reference.

ACKNOWLEDGMENT OF GOVERNMENT SUPPORT

This invention was made with Government support under SBIR contract N68335-06-C-0372, awarded by the US Navy. The government has certain rights in the invention.

BACKGROUND OF THE INVENTION

Field of the Invention

The invention pertains to the field of communications earplugs. More particularly, the invention pertains to a wireless earplug for use with a magnetic induction communications system.

Description of Related Art

It is well documented in literature that the use of double hearing protection (earmuff and earplug) is superior in providing noise attenuation compared to using only one hearing protection device alone. Often communications are also necessary, and thus, a communications earplug is used.

U.S. Pat. No. 4,972,491, "Ear-Mic Headseat/Eardefender" shows such an arrangement where earplugs within earmuffs/headset are hard-wired to a headset cord. This is discussed in the June, 2000, issue of the Journal of the Audio Engineering Society in an article entitled "Development of the Wireless Communications Earplug for Application in Military Aviation (Van Wijngaarden et al, *J. Audio Eng. Soc.*, Vol. 48, No. 6, pp. 553-558).

The problem with typical communications earplugs is that they employ wires to provide the communications signal, and the problems with using wires are manifold.

Inductive coupling for communications is known to the art. For example, see U.S. Pat. No. 2,268,665, "Method and Arrangement for Transferring Telephone Conversations to Other Electrical Devices" which is a cradle for telephone handset which picks up sound by inductance, or U.S. Pat. No. 3,322,897, "Coil Pick-up and Tube Recorder System" which uses circular loop pickup around handset earpiece to pick up telephone signals for a recorder.

Inductive coupling is commonly used between a telephone handset and a hearing aid. This application is often referred to as a "T-coil". For examples, see U.S. Pat. No. 2,530,621, "Wearable Hearing Aid with Inductive Pick-Up for Telephone Reception", or U.S. Pat. No. 5,796,821, "Hearing aid telephone interconnect system".

U.S. Pat. No. 3,125,646, "Electromagnetically Coupled Hearing Aid" couples an amplified signal from a sound input unit in eyeglasses or headband to a sound output unit in user's ear.

U.S. Pat. No. 5,420,930, "Hearing aid device" uses a receiver assembly having a flexible coil shape worn in the outer portion of the auditory canal with a small transducer that extends into the auditory canal, and a transmitter assembly. The receiver is driven by magnetic induction from the transmitter assembly positioned a few inches away, as in a neck pendant. Similarly, in U.S. Pat. No. 6,208,740, "Stereophonic magnetic induction sound system" the user wears a necklace with transmitter which transmits sound inductively to active receiver units in ears.

US Published Patent Application 2004/151,334, "Actuator for an active noise control system" is an in-ear transducer for use in ANR systems with several embodiments, all including permanent magnets, diaphragms and voice coils.

US Published Patent Application 2005/18,859, "Optically Driven Audio System" shows an alternate system of earmuffs/in-ear earplug using optical transmission from transmitters to active receivers.

SUMMARY OF THE INVENTION

The invention provides an improved wireless communications earplug for use with a magnetic field transmitter comprising a loop of wire surrounding the pinna of a user's ear or other transmitters that generate a magnetic field. The wireless earplug has a receiver made of a coil of wire on a magnetic bobbin, mounted in close proximity or in contact with a magnetic case of a speaker. The magnetic case of the speaker serves to increase the magnetic flux through the receiver and improves the efficiency of the earplug. The speaker is acoustically coupled to an eartip, and the earplug may be molded into a custom earplug body.

DETAILED DESCRIPTION OF THE INVENTION

A wireless magnetic induction communications system was previously described in co-pending patent application entitled "Wireless Communications Headset System Employing a Loop Transmitter That Fits Around the Pinna, U.S. Ser. No. 11/837,129, filed Aug. 10, 2007, and published on Feb. 12, 2009, as US2009/0041285. That application, incorporated herein by reference, describes a wireless magnetic induction communications system. Wireless earplugs are advantageous compared to wired earplugs because there is no communications cable which can be snagged on objects during use which can rip the earplug out of the ear causing pain and loss of communications. Communications wires are cumbersome and also create acoustic leaks when the cables pass between the skin and an earmuff ear cushion. In the present invention a battery is preferably not used to power the wireless earplug, and therefore communications will not be interrupted due to battery failure. In addition, small batteries are relatively expensive.

If acoustic dampers are used in the sound delivery duct, debris is prevented from getting into the earplug, including fluids at lower pressures. The invention does not require active electronics that can fail in the field and be damaged by electro-static discharge; hence, the invention is very reliable and robust.

Figure 1:
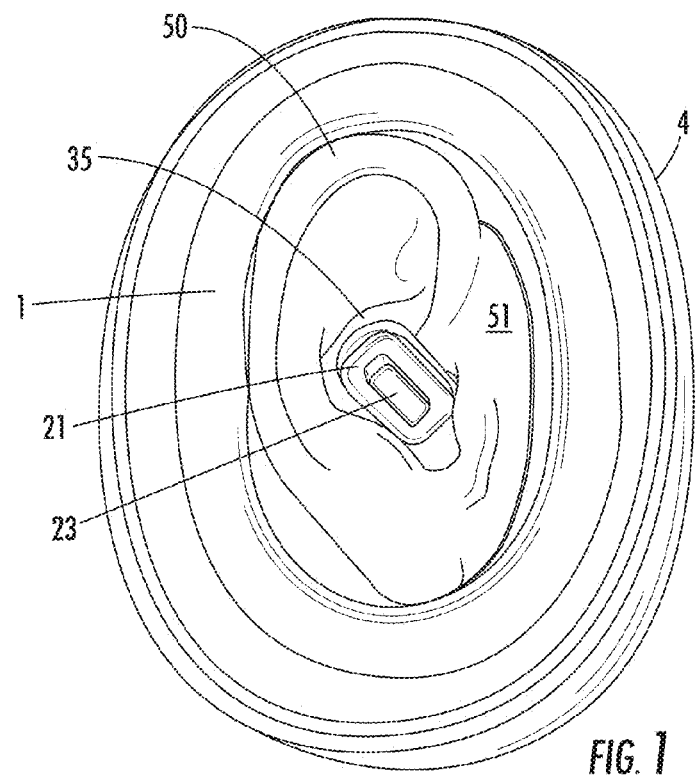
FIG. 1 shows a transmitter coil mounted behind an ear cushion and a wireless communications earplug.

As shown in FIG. 1, an embodiment of a magnetic induction wireless communications system includes a loop transmitter and a loop or coil receiver. The loop transmitter is used to generate a magnetic field, while the loop receiver converts the magnetic field to a voltage which is input to a speaker in a communications earplug. Novel features of the system are that it operates at audio frequencies, generates essentially no radio frequency interference, is compact, and requires no battery in the communications earplug.

A transmitter coil 1 mounted behind an ear cushion 4 and a wireless communications earplug 35 (with back cover removed) is shown in FIG. 1. The earplug cover is removed exposing the receiver coil 21 and speaker 23 locations. The transmitter is located behind the ear cushion 4 of a headset (headset not shown). The ear cushion 4 and transmitter 1 both fit around the pinna 50 of an ear (here shown as artificial ear 51, a model generally in the size and shape of a human ear, of a type often used in acoustical testing laboratories).

Figure 2:
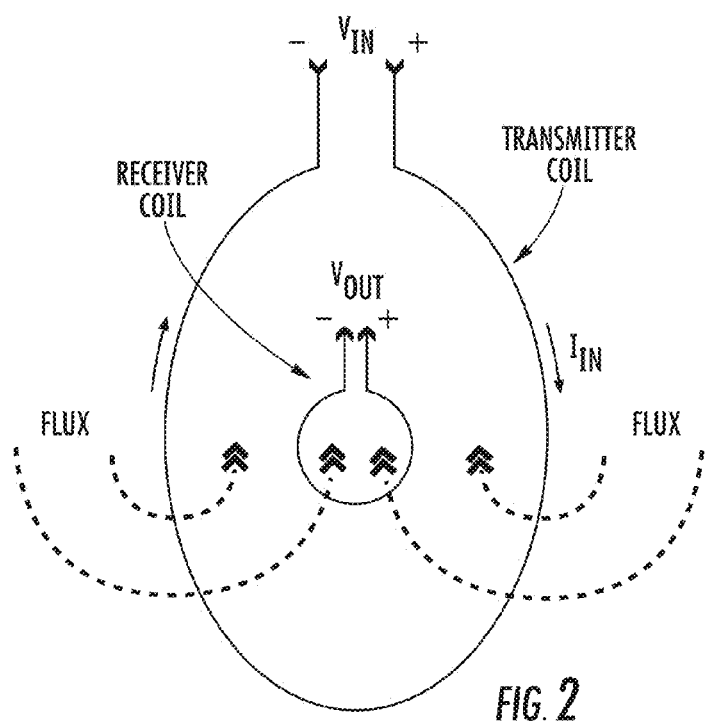
FIG. 2 shows a schematic of the relationship between transmitter and receiver coils.

As shown schematically in FIG. 2, voltage $V_{in}$ applied to the transmitter coil generates current $i_{in}$ which generates a field of magnetic flux, and the field is converted to a voltage $V_{out}$ by a receiver coil. The receiver coil voltage, $V_{out}$, is input to a speaker (not shown in the figure). In this way, audio-frequency signals can be transmitted to a speaker in a wireless manner without the use of a battery in the communications earplug.

Figure 3:
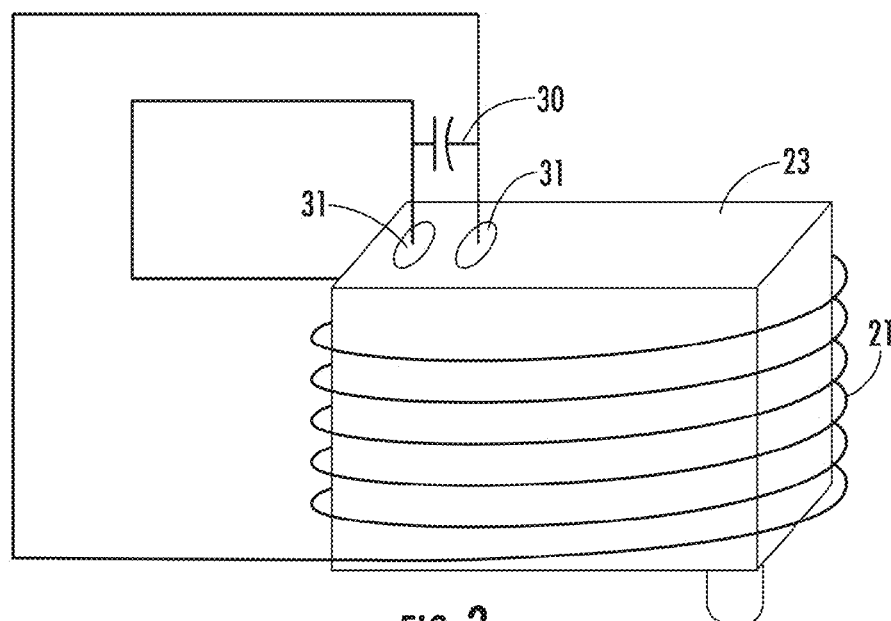
FIG. 3 shows a speaker located within receiver coils.

As shown in FIG. 3, in the Ser. No. 11/837,129 invention, the receiver coil wire 21 is wrapped around the earplug communications speaker 23. This geometry was used to minimize the physical volume of the device. If the speaker is made of magnetic material, which is typically the case with hearing aid speakers, the speaker acts as a magnetic core which focuses the magnetic field through the coils and results in significantly improved sensitivity.

Figure 4:
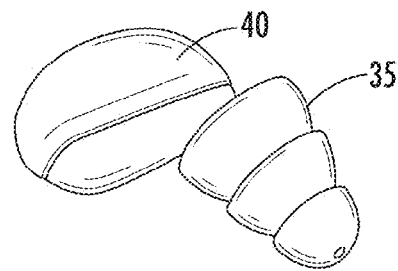
FIG. 4 shows an example of a wireless earplug using a loop receiver.

In FIG. 4, an example of a wireless earplug 40 is seen with a rubber flange eartip 35 (other types of eartips, such as foam, may be used).

Figure 5:
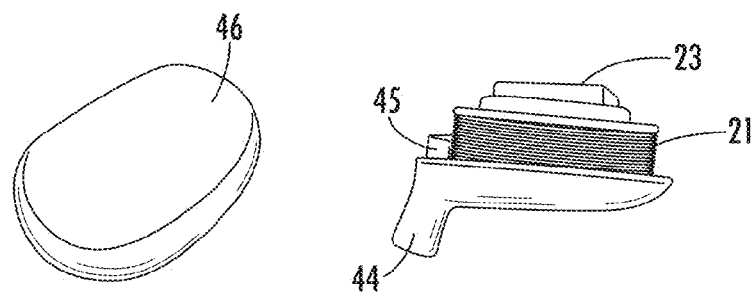
FIG. 5 shows the earplug of FIG. 4 with the lid and eartip removed.

In FIG. 5, the lid 46 of earplug 40 shown in FIG. 4 has been removed to show the components of the wireless communications earplug. A loop receiver 45 comprises a coil 21 wrapped around a speaker 23. Sound generated by the speaker 23 is routed through a nipple 44, and thus into the eartip 35. The eartip 35 has a channel through its center that provides an acoustical path which allows sound to be transmitted from speaker 23 to the user's ear canal.

Figure 6:
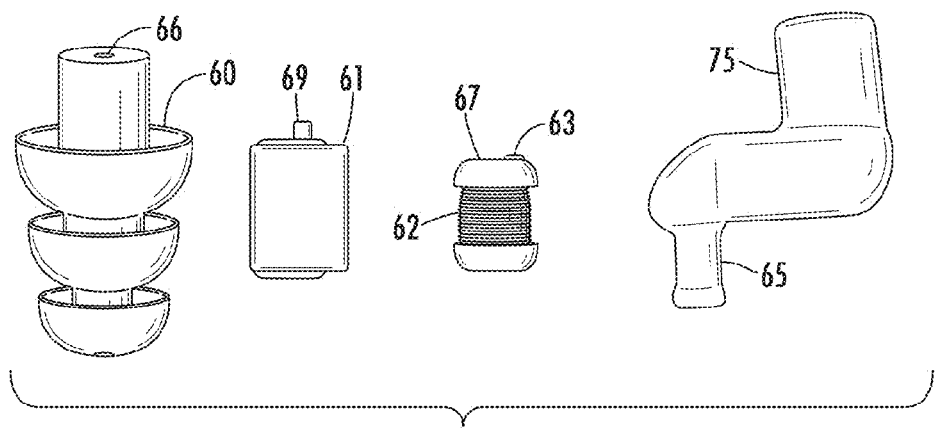
FIG. 6 shows elements of a wireless earplug, with a dime for scale.

The basic elements of an improved wireless earplug of the present invention are shown in FIG. 6.

From left to right are an eartip 60, speaker 61, a receiver 67 comprising a coil 62 wrapped around a magnetic material bobbin 63, and earshell 75. The speaker 61 has a sound port 69 where sound generated by the speaker 61 exits the speaker 61. The sound port 69 is acoustically coupled to a nipple 65 of the earshell 75. A dime is included in FIGS. 6 through 13 to indicate size, although it will be understood that the size of the components may be varied within the teachings of the invention.

The eartip 60 shown is a rubber triple-flange type; however, there are many other types of eartips commonly used for communications earplugs that could be employed, such as single-flange rubber, foam, and custom-fit types. The eartip 60 is mounted to the nipple 65 of the earshell 75 to provide a full or partial seal between the nipple 65 and an ear canal to generally prevent ambient noise from entering the ear canal. The eartip 60 has a sound delivery tube or channel 66 running through its center to allow the acoustic signal from the speaker 61 to be delivered to the ear canal to provide communications.

Figure 7:
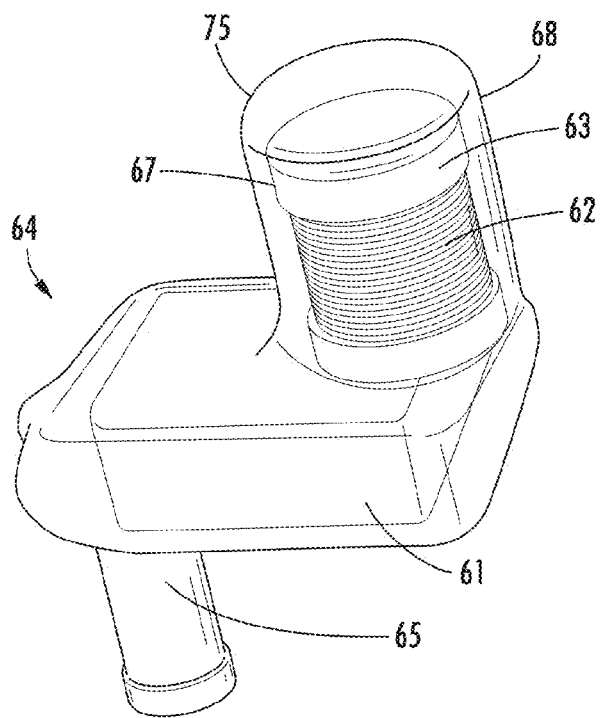
FIG. 7 shows a wireless earplug with speaker and coil installed.
Figure 8:
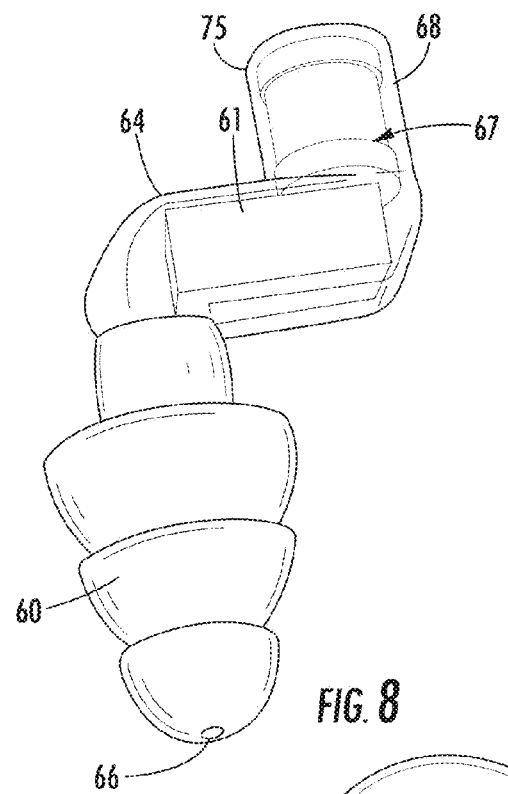
FIG. 8 shows a wireless earplug shell with flange eartip attached.

In FIG. 7 the speaker 61 and receiver 67 are installed in the earplug 64 and the back 68 of the earshell 75 is attached. The earplug 64 with a rubber flange eartip 60 attached is shown in FIG. 8. As stated earlier, many other communications eartips can be attached to the communications earplug.

Figure 9:
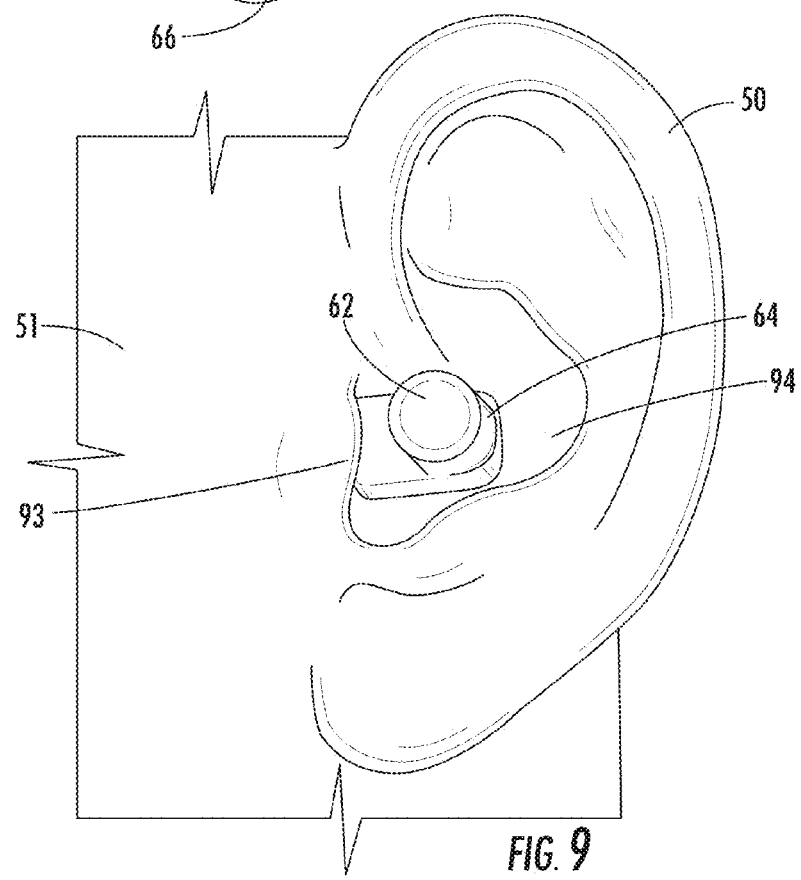
FIG. 9 shows a wireless earplug in an artificial ear.

The communications earplug 64 as it fits in an artificial ear 51 can be seen in FIG. 9. The eartip 60 and nipple fit into the ear canal, while the rest of the earplug generally forms an L shape geometry within the concha 94. One can see that the L-shape of the earplug 64 allows it to fit under the tragus 93 while the receiving coil 62 fits in the concha 94 area without causing pressure points in the ear. This design results in superior comfort compared to design geometries that contact the tragus 93 and/or concha 94 side wall. The L-shape also prevents the earplug from being inserted too deeply and facilitates correct receiver orientation relative to the transmitter coil, not shown in this figure, which can surround the pinna 50 in the system shown in FIG. 1 or can be otherwise configured and located so as to generate a field of magnetic flux through the receiver 67.

Figure 10:
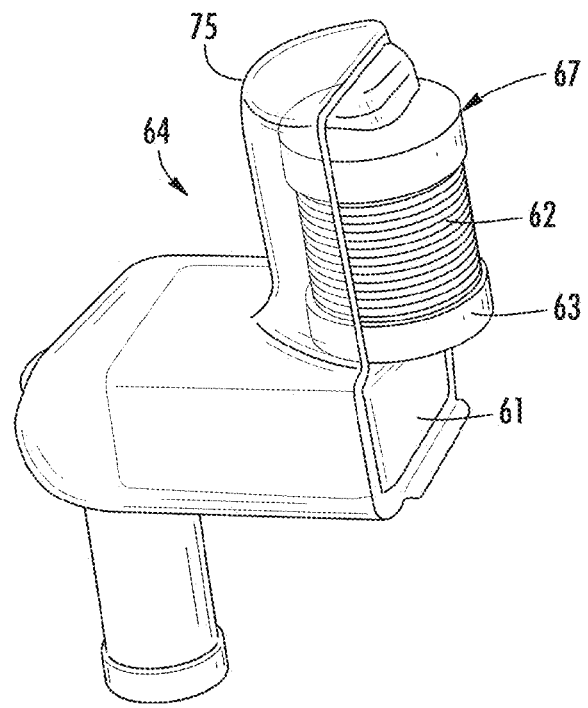
FIG. 10 shows the view of FIG. 7 with the back of the earshell removed.

In FIG. 10 the speaker 61 and receiver coil 62 are installed in the earplug 64. The back of the earshell 75 has been removed so that the speaker 61 and coil 62 and bobbin 63 of the receiver 67 can be seen. Although not seen in the photo, the wires from the receiver 67 coil 62 should be electrically connected to the speaker 61. As stated earlier, the magnetic field through the coil 62 generates a voltage which is used to drive the speaker 61.

The receiver 67 is installed so that it is in close proximity to the speaker 61, and makes physical contact with the speaker 61 in the preferred embodiment. A very small gap (less than 0.005 in) between the receiver 67 and speaker 61 won't affect the sensitivity of the communications earplug appreciably, but larger gaps will. The speaker 61 casing, when made of magnetic material, acts to increase the flux lines through the coil 62 and increases the effective inductance of the coil 62. The most effective orientation of the speaker 61 relative to the magnetic bobbin 63 is one that will help to increase the lines of magnetic flux through the magnetic bobbin 63.

Figure 11:
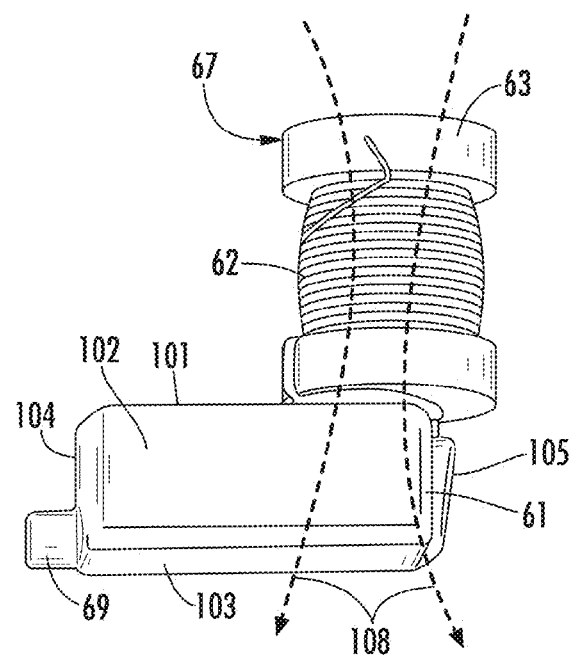
FIG. 11 shows speaker and receiver orientation, off-center.

FIG. 11 shows the speaker 61 and receiver 67 coil 62 orientation when mounted in the earshell (not shown in this figure). The coil 62 wires are electrically connected to the speaker 61 to provide the communications electrical signal. As previously discussed, the receiver 67 employs a coil 62 of wire wrapped around a magnetic bobbin 63. Transformer wire has been found to work well for the coil 62, and magnetic ceramic material has been found to work well for the bobbin 63.

The speaker 61 casing is preferably at least partially made of a magnetic metal material. If the speaker casing as manufactured is not made of a magnetic metal material, it can be placed inside a small enclosure made of magnetic metal material, creating a magnetic metal speaker casing. The top surface 101 of the speaker 61 casing that is in close proximity to the receiver 67, should be made of magnetic material. Additionally, side surfaces 102 of the speaker 61 casing, front end surface 104, and back end surface 105 should be made of magnetic material to the extent possible. The top 101 sides 102 and ends 104 and 105 provide a low-reluctance path for the magnetic field flux lines 108 that pass through the receiver 67, which improves the efficiency of the earplug. It is less important that a bottom surface 103 of the speaker 61 casing be made of magnetic material. If an enclosure is used around the speaker 61, a hole needs to be provided for the sound port 69 of the speaker where sound exits the speaker 61. The speaker 61 orientation relative to the receiver 67 can change, but the orientation of the speaker 61 with receiver 67 and speaker 61 surfaces should be chosen to ensure that flux lines are directed through the receiver 67 and not around the receiver 67 in a shunting manner.

The amount of copper used for the coil 62 should be maximized while keeping the overall size of the device within reasonable limits to fit in an ear. The size of the wire and number of turns in the coil 62 when wound on magnetic bobbin 63 and mounted upon speaker 61 are also chosen to generally match the electrical impedance of the speaker 61 to achieve high efficiency. A ceramic magnetic bobbin 63 wound with a coil 62 comprising 500 turns of 40 AWG transformer wire yields a resistance of 22 ohms and inductance of 6.8 mH, which has been found to work well with a 22 ohm 3.0 mH hearing aid speaker made by Knowles of Itasca, Ill. The speaker 61 used in this invention is small, efficient, and employs a casing made of magnetic material. When placed in contact with the speaker 61, the effective inductance of this example receiver coil 62 increases to 8.4 mH.

Preferably, the magnetic receiver 67 and bobbin 63 should be as close as possible to the speaker 61. If the receiver 67 bobbin 63 and speaker 61 are spaced with only a 0.03 inch gap apart, a loss of 2 dB in sensitivity results, compared to when the bobbin 63 and speaker 61 are touching, and the system requires 58% more power for the same output level. The loss in sensitivity becomes 3.5 dB when the speaker 61 and receiver 67 are far apart.

The sensitivity of the earplug of the present invention is approximately 5 dB higher than the design of prior application Ser. No. 11/837,129 shown in FIG. 5 and requires 68% less power for the same output level. Due to the improvement in sensitivity of the wireless system, the transmitter can be located a further distance (approximately 0.75 in) away from the communications earplug with the same sensitivity. In addition, the new L-shaped design geometry orientation results in a better physical fit in the human ear.

Figure 12:
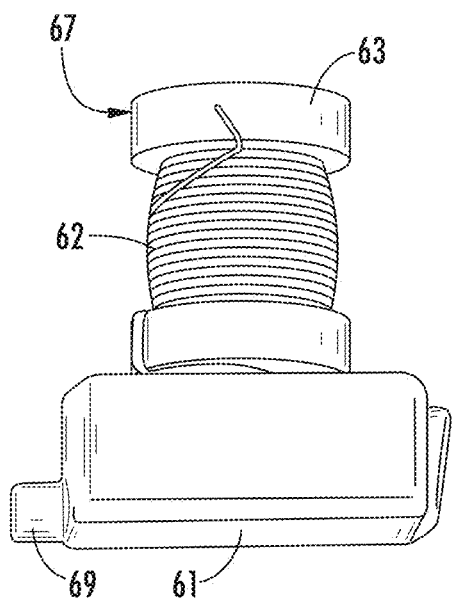
FIG. 12 shows speaker and receiver orientation, on-center.

FIG. 12 shows another configuration of the speaker 61 and receiver 67. In this configuration, the receiver 67 is centered over the speaker 61. The resulting sensitivity is slightly higher than in the configuration of FIG. 11. As before, it is preferable that the receiver 67 bobbin 63 and speaker 61 casing are as close as possible, preferably touching. The sound port 69 of the speaker 61 is pointing to the left in the previous photos; however, other designs with the sound port 69 facing other directions will work as well. In addition, the speaker 61 orientation may change; however, the speaker 61 and receiver 67 should be located as close as possible to each other and be oriented to draw the lines of magnetic flux through the bobbin 63 to yield the highest efficiency.

An element that can be added to the communications earplug 64 includes an acoustic damping element located in the earshell nipple 65 eartip 60, sound port 69 or other location in the acoustic path. Acoustic damping elements are often used in communications earplugs and hearing aids. They dampen resonances in the acoustic response and are often implemented using screen material or foam. These dampers also prevent earwax and debris from entering the earshell and damaging the speaker 61.

Electronic equalization can also be used in between the receiver coil 62 and speaker 61 to shape the frequency response of the earplug 64. For example, as shown in FIG. 3, a capacitor 30 can be installed in parallel with the coil 21 and speaker terminals 31 to boost the frequency response at select frequencies, such as the region around 3 kHz. A 1 µF capacitor wired in parallel with the receiver and speaker is effective for boosting the 3 kHz region when using the receiver described above. Other passive equalization networks may be used to tailor the response of the system.

Figure 13:
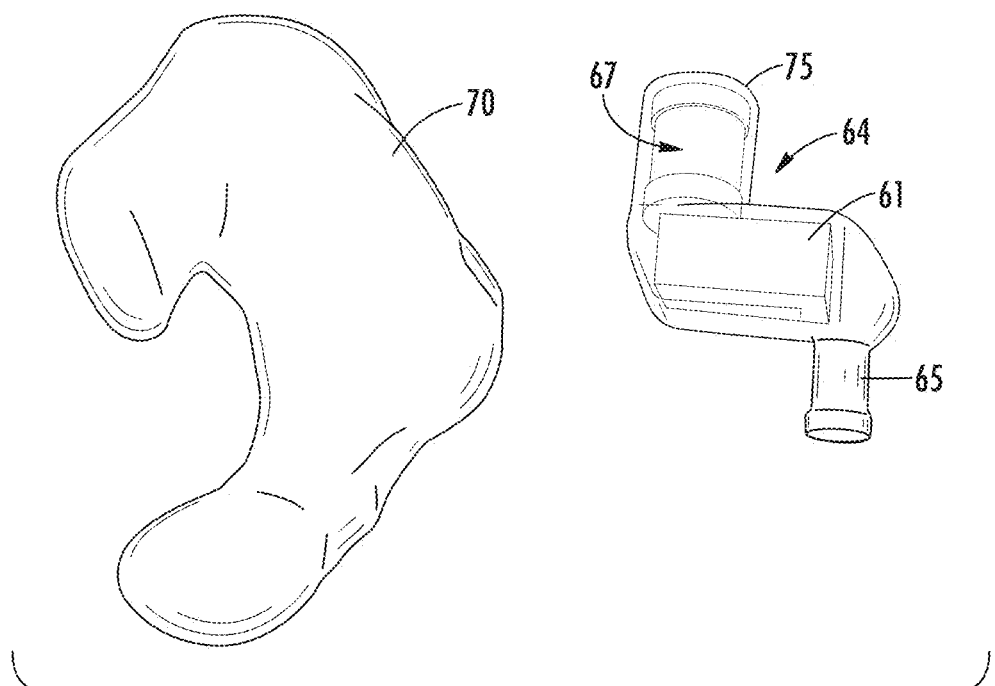
FIG. 13 shows a molded silicone earplug and wireless earplug.

The new geometry enables the earplug to be used alone as a generally universal-fitting earplug, or embedded in a custom-molded earplug body. FIG. 13 shows a custom-molded earplug body 70 and the wireless earplug 64 of the invention, with a dime for size reference. The custom-molded earplug body 70 may be made of silicone, vinyl, acrylic and other materials that range from soft to hard.

Figure 14:
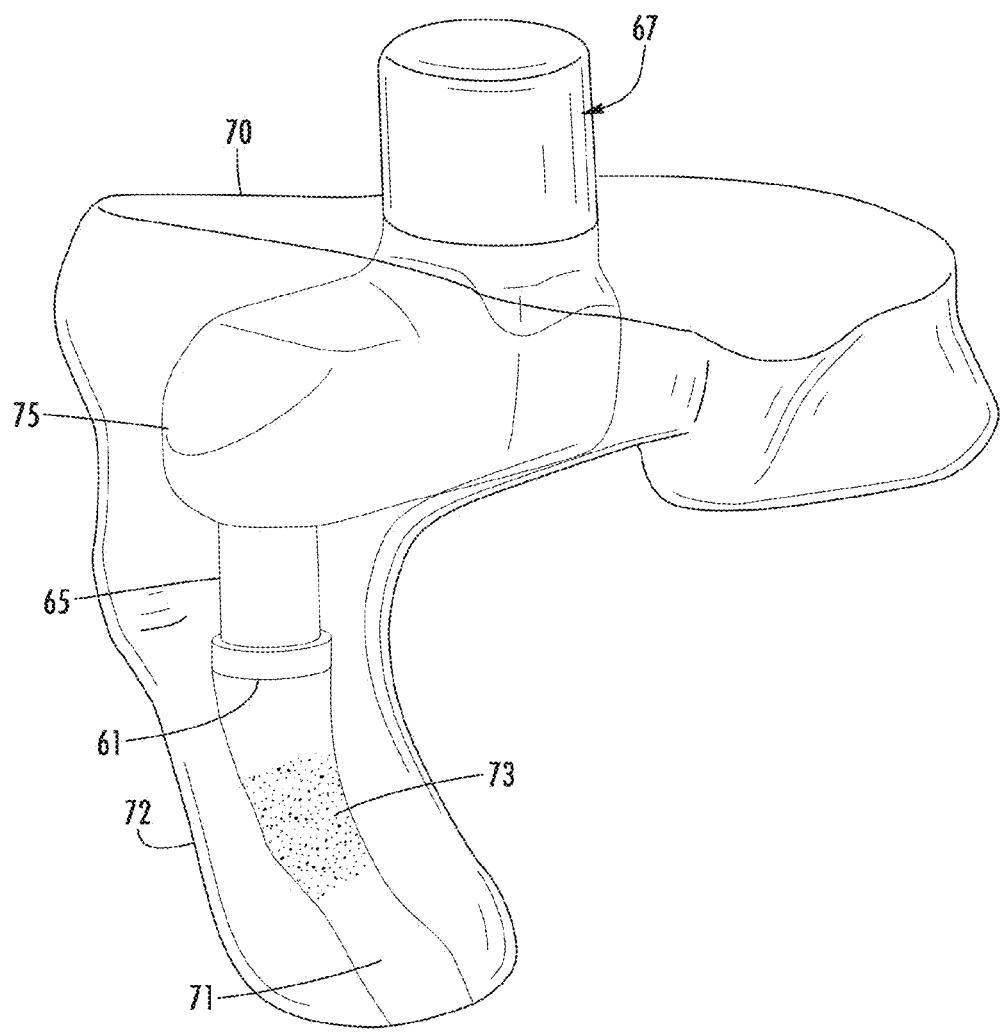
FIG. 14 shows a molded earplug with embedded wireless earplug shell.

FIG. 14 shows the wireless earshell 75 as it could be embedded in the custom-molded earplug body 70. The receiver 67 stands proud of the body 70, but will not contact any part of the ear because it extends in the concha region of the ear. The rest of the earshell 64 is fully embedded within the custom-molded earplug body 70.

When constructing this custom-molded earplug body 70, one needs to remove a region 71 within the portion 72 of the body 70 that extends into the ear canal to provide a sound delivery path. This is commonly done in a custom-molded communications earplug. The sound delivery path 71 must reach the sound port 69 of the speaker 61 so that an acoustic path exists from the speaker 61 to the interior of the user's ear canal.

The earshell 75 nipple 65 may be shortened, and/or the angle of the nipple 65 to the custom-molded earplug body 70 may be changed for a better fit. In addition, the nipple 65 may be eliminated and the sound path 71 through the custom-molded plug body 70 may extend to an opening in the body of the earshell to provide the sound delivery path. Acoustic damping material 73 can be used in the sound delivery path to dampen acoustic peaks in the frequency response.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A wireless communications earplug for use with a magnetic field transmitter, comprising:
   a) a receiver comprising a coil of wire wound upon a bobbin of magnetic material; and
   b) a speaker having a case at least partially made of magnetic material, an acoustic output and an electrical input coupled to the wire of the receiver;
   wherein the bobbin of the receiver is mounted in sufficiently close proximity to the case of the speaker such that a measured inductance of the coil of the receiver is increased compared to an inductance of the coil of the receiver when the receiver is not mounted to the speaker, and the receiver is oriented such that flux lines passing through the speaker are directed to pass through the coil of the receiver.

2. The earplug of claim 1, in which the bobbin of the receiver is mounted within 0.03 inches of the case of the speaker.

3. The earplug of claim 2, in which the earplug further comprises a molded earshell having a body encasing at least the speaker, and the eartip forms part of the molded earshell.

4. The earplug of claim 1, further comprising an eartip for insertion into a user's ear canal, acoustically coupled to the acoustic output of the speaker.

5. The earplug of claim 1, in which the bobbin of the receiver is in contact with the case of the speaker.

6. The earplug of claim 1, in which the receiver is centered upon the case of the speaker.

7. The earplug of claim 1, in which the acoustic output of the speaker is adjacent to an end of the speaker, and the receiver is mounted upon the case of the speaker at an opposite end from the acoustic object, such that the receiver and the speaker form an L shape.

8. The earplug of claim 1, further comprising an acoustic damping element coupled to the acoustic output of the speaker.

9. The earplug of claim 1, further comprising a passive electronics circuit coupled to the coil and to the speaker.

10. A wireless communications earplug, comprising:
    a) a receiver comprising a coil of wire wound upon a bobbin having an axis;
    b) a speaker having an acoustic output and an electrical input connected to the coil of wire of the receiver; and
    c) an eartip for insertion into a user's ear canal, acoustically coupled to the acoustic output of the speaker;
    wherein the speaker is located at least partially under the tragus and the receiver is located at least partially in the concha of a human ear, with the axis of the bobbin being oriented parallel to an axis of a portion of the ear canal into which the eartip is inserted.

11. The earplug of claim 10, in which the earplug further comprises a molded earshell having a body encasing at least the speaker, and the eartip forms part of the molded earshell.

12. The earplug of claim 10, in which the acoustic output of the speaker is adjacent to an end of the speaker, and the receiver is mounted upon the case of the speaker at an opposite end from the acoustic object, such that the receiver and the speaker form an L shape.

13. The earplug of claim 10, further comprising an acoustic damping element coupled to the acoustic output of the speaker.

14. The earplug of claim 10, further comprising an equalization circuit connected across the coil and speaker.

15. A communications system comprising:
    a) a magnetic field transmitter for transmitting in the audio frequency spectrum;
    b) a receiver comprising a coil of wire wound upon a bobbin;
    c) a speaker having an acoustic output and an electrical input coupled to the wire of the receiver; and
    d) an eartip for insertion into a user's ear canal, acoustically coupled to the acoustic output of the speaker
    wherein the speaker is located at least partially under the tragus and the receiver is located at least partially in the concha of a human ear, with the axis of the bobbin being oriented parallel to an axis of a portion of the ear canal into which the eartip is inserted, and the speaker is connected to the receiver through passive electrical components.

16. The system of claim 15, in which the earplug further comprises a molded earshell having a body encasing at least the speaker, and the eartip forms part of the molded earshell.

17. The system of claim 15, in which the bobbin of the receiver is in contact with the case of the speaker.

18. The system of claim 15, in which the receiver is centered upon the case of the speaker.

19. The system of claim 15, in which the acoustic output of the speaker is adjacent to an end of the speaker, and the receiver is mounted upon the case of the speaker at an opposite end from the acoustic object, such that the receiver and the speaker form an L shape.

20. The system of claim 15, further comprising an acoustic damping element coupled to the acoustic output of the speaker.

21. The system of claim 15, further comprising an equalization circuit coupled to the coil and to the speaker.

22. The system of claim 15, in which the magnetic field transmitter comprises a coil of wire having an open center sized to fit around a pinna of a user's ear.

* * * * *